(12) United States Patent
Hofmann et al.

(10) Patent No.: US 6,330,466 B1
(45) Date of Patent: *Dec. 11, 2001

(54) USING A MULTI-ELECTRODE PROBE IN CREATING AN ELECTROPHYSIOLOGICAL PROFILE DURING STEREOTACTIC NEUROSURGERY

(75) Inventors: Ulrich G. Hofmann; John H. Thompson; David T. Kewley, all of Pasadena, CA (US)

(73) Assignee: California Institute of Technology, Pasadena, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/256,685

(22) Filed: Feb. 23, 1999

Related U.S. Application Data

(60) Provisional application No. 60/075,741, filed on Feb. 23, 1998.

(51) Int. Cl.[7] .................................................. A61B 5/042
(52) U.S. Cl. .......................... 600/378; 600/544; 607/116
(58) Field of Search ................................... 600/378, 544; 607/116, 139; 606/130

(56) References Cited

U.S. PATENT DOCUMENTS

| 4,245,645 | * | 1/1981 | Arseneault et al. | 600/378 |
|---|---|---|---|---|
| 4,461,304 | * | 7/1984 | Kuperstein | 600/378 |
| 5,524,338 | * | 6/1996 | Martyniuk et al. | 29/825 |
| 5,692,516 | * | 12/1997 | Kaneko et al. | 600/544 |
| 5,843,093 | * | 12/1998 | Howard, III | 606/130 |
| 5,843,148 | * | 12/1998 | Gijsbers et al. | 607/116 |
| 5,928,143 | * | 7/1999 | McNaughton | 600/373 |
| 6,011,996 | * | 1/2000 | Gielen et al. | 607/116 |
| 6,128,527 | * | 10/2000 | Howard, III et al. | 600/544 |

OTHER PUBLICATIONS

Sahani et al., On the Separation of Signals from Neighboring Cells in Tetrode Recordings, 1997, Advances in Neural Information Processing Systems 10, pp. 222–228.

* cited by examiner

*Primary Examiner*—Lee S Cohen
(74) *Attorney, Agent, or Firm*—Fish & Richardson P.C.

(57) ABSTRACT

A multi-electrode probe is used to create an electrophysiological depth profile during stereotactic neurosurgery. A surgeon uses CT or MRI images to identify the general location of a target site in the brain and then inserts the multi-electrode probe into this area. Each electrode on the probe produces a signal that indicates the level of activity in a nearby neuron or cluster of neurons. A processor converts these signals into an electrophysiological depth profile indicating the level of activity detected by each of the electrodes. The surgeon identifies the precise location of the target site by watching the display to determine which electrode or group of electrodes detects the highest level of neuronal activity as the stimulus is provided.

23 Claims, 3 Drawing Sheets

USING A MULTI-ELECTRODE PROBE IN CREATING AN ELECTROPHYSIOLOGICAL PROFILE DURING STEREOTACTIC NEUROSURGERY

CROSS REFERENCE TO RELATED APPLICATIONS

This application claims the benefit of U.S. Provisional Application No. 60/075,741, filed on Feb. 23, 1998.

TECHNOLOGICAL FIELD

This application relates to the use of electrode probes in stereotactic neurosurgery.

BACKGROUND

Certain neurosurgical procedures require the determination of the precise location of target tissue, and fine discrimination of the target from adjacent non-target tissue. For example, during a "pallidotomy," a procedure often performed on patients with Parkinson's disease, the neurosurgeon must carefully introduce a lesioning device into a small area deep in the brain called the Globus pallidus internus (Gpi), while avoiding the adjacent Globus pallidus externus (Gpe). Computed tomography (CT) and magnetic resonance imaging (MRI) are typically used to guide the surgeon to the Gpi/Gpe region. More precise, localized targeting is often achieved by means of electrophysiological localization techniques.

Conventional electrophysiological localization techniques typically involve the insertion of a tungsten electrode into the brain to detect neural activity. Because different brain areas produce characteristic patterns of neural activity, the signals picked up by the electrode at different locations are used to finely distinguish between the different brain areas. The Gpe and Gpi, for example, produce different characteristic patterns of activity, as monitored on the tungsten electrode. This knowledge is used during a pallidotomy to determine the boundary between the two structures, which allows the subsequent introduction of a lesion into the Gpi while avoiding lesioning the Gpe.

Because the tungsten electrode detects activity at only one site in the brain at any given time, the surgeon moves the electrode sequentially to multiple sites, stopping at each site for some time to monitor the local neuronal activity. Typically the electrode is inserted into the brain at a few different surface locations, and several depth locations are monitored along each electrode insertion track. Characteristic patterns of neural activity are noted at several of these electrode locations. As this information builds up over the course of the surgery, the surgeon derives an anatomical and/or functional map of that part of the brain.

The success of electrophysiological localization depends largely on the skill of the surgeon, who must accurately position the electrode at several sites in the brain and then accurately interpret the measurements taken by the electrode. Even the slightest misguidance of the electrode or misinterpretation of the measurements can lead to brain damage. As the number of monitored sites increases, so does the time required, and therefore the risk of brain damage, the cost of surgery, and the risk to the patient's health.

SUMMARY

The inventors have developed a technique for using a multi-electrode probe to rapidly create an electrophysiological depth profile during stereotactic neurosurgery. The depth profile provides information about concurrent neuronal activity at a set of positions, or depths, along the probe insertion track. This information supplants the limited information that neurosurgeons currently receive by taking a set of individual measurements at multiple depth positions with a single-electrode probe, and then manually assembling the sequentially-obtained information into a composite depth profile. One measurement with the multi-electrode probe allows the derivation of a depth map that normally is possible only with many measurements using a single-electrode probe, thus saving surgical time and reducing the associated costs and risks. Simultaneous measurement at multiple locations, which is impossible with single-electrode probes, also provides information about correlations between different neural groups. This information is useful in improving the quality of data interpretation and surgical targeting.

In one aspect, the invention features a technique for using a multi-electrode probe to locate a target site in a brain during stereotactic neurosurgery. The surgeon first identifies an area of a brain that includes a target site to be treated. The surgeon then inserts a multi-electrode probe into this area of the brain. The probe includes multiple electrodes that concurrently produce output signals indicative of concurrent neuronal activity at multiple sites in the brain. The output signals are used to generate a user interface that provides an indication of the level of concurrent neuronal activity at each of the multiple sites.

In another aspect, the invention features a multi-electrode probe system for use in locating a target site in a brain during stereotactic neurosurgery. The system includes a multi-electrode probe inserted into an area of a brain that includes a target site to be treated. The probe includes multiple electrodes that produce output signals indicative of concurrent neuronal activity at multiple sites in the brain. The system also includes a processor that receives the output signals from the electrodes and derives the level of concurrent neuronal activity that occurs at each of the multiple sites. A user interface displays an indication of the level of concurrent neuronal activity at each of the multiple sites.

In some embodiments, the user interface provides a depth profile indicating the level of concurrent neuronal activity at various depths in the brain. Some versions of the user interface provide an indication of spike rate for individual neurons at the multiple sites. The user interface often includes a graphical display or a sound signal that provides a visual or audible indication, respectively, of the level of neuronal activity at each of the multiple sites. Other embodiments require the surgeon to provide a stimulus directed to neurons at the target site to increase the level of neuronal activity at the target site.

DETAILED DESCRIPTION

Figure 1:
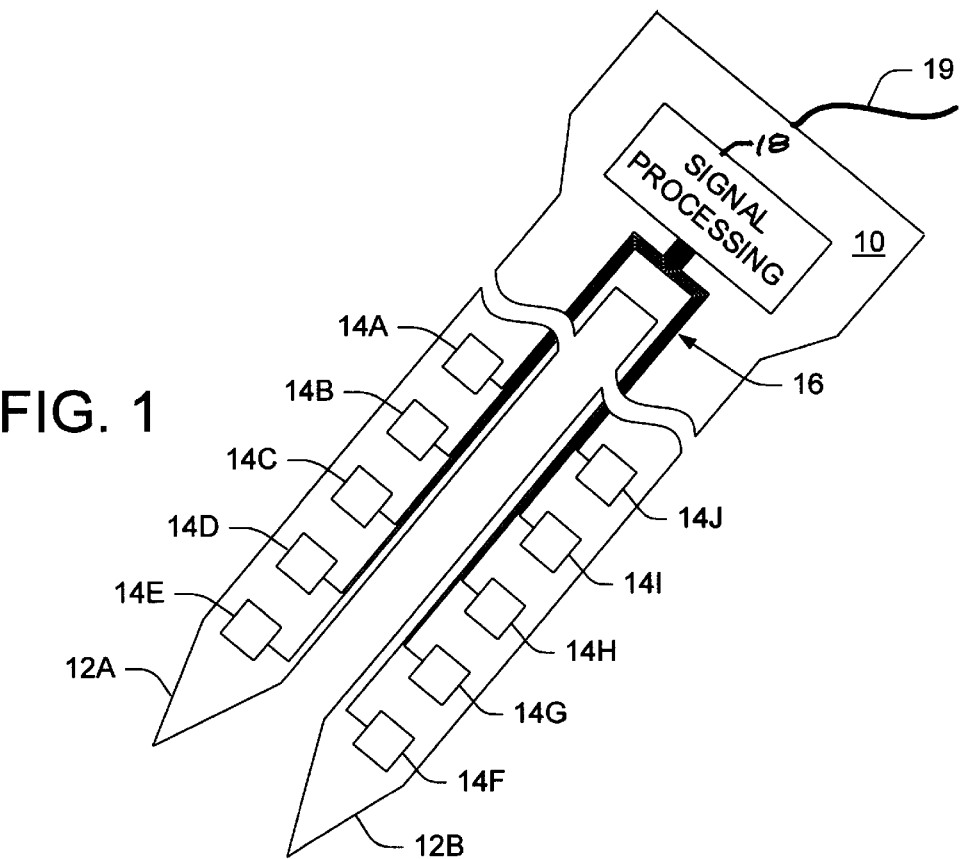
FIG. 1 shows a multi-electrode probe for use in stereotactic neurosurgery.

FIG. 1 shows a multi-electrode probe 10 that is used in locating a target site in the brain during stereotactic neurosurgery. The probe 10 includes one or more relatively thin shafts 12A–12B that penetrate the brain. Each shaft 12A–12B includes an array of spaced electrodes 14A–J that detect activity in the neurons of the brain. This activity generally appears in the form of current spikes in the neurons. These current spikes produce corresponding voltage spikes, or event potentials, in the matter surrounding the neurons. The electrodes 14A–J detect these event potentials and produce continuous output voltages that vary in magnitude as the event potentials are detected. Because the probe 10 includes an array of electrodes 14A–J, the probe 10 is able to detect concurrent activity at multiple sites in the brain.

A group of conductors 16 on the probe link the electrodes 14A–J to an optional signal processing circuit 18. This circuit 18 includes conventional signal processing electronics, such as amplifying, filtering, and digital signal processing (DSP) circuitry, that prepare the electrode signals for external processing. The probe 10 also includes a signal transmission element, such as a conductive cable 19 or an infrared (IR) transmitter, that delivers the signals to an external processor (described below).

The probe shafts 12A, 12B serve several functions, such as providing structural support for the electrodes and the signal conductors. The probe shafts 12A, 12B are manufactured from a combination of structural, conductive, and insulating materials, such as silicone, polyimide, glass, epoxy, tungsten, and gold. The electrodes 14A–J are manufactured from any of a variety of materials that conduct electrically, including metals such as tungsten and gold, metal compounds such as iridium oxide, polymers such as polyimide and silicone, and semiconductors such as doped silicon. One technique for manufacturing the probe 10 is the silicon-based micromachining technique described in Kewley, et al., "Plasma-etched Neural Probes," Sensors and Actuators A 58 (1997), pp. 28–35, the full disclosure of which is incorporated by reference.

In general, the probe 10 is manufactured with dimensions tailored to the specific part of the brain in which the probe 10 is to be used. For example, one probe design, for use in performing a pallidotomy on a typical human brain, includes a single shaft that is approximately 190–250 mm long and has a linear array of thirty-two electrodes separated from each other by approximately 40 $\mu$m near the tip of the shaft.

Figure 2:
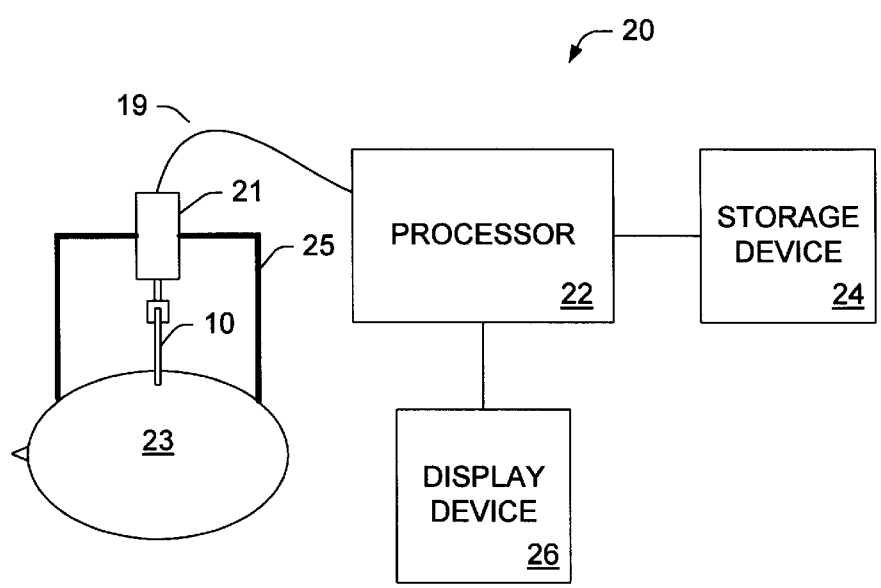
FIG. 2 shows a multi-electrode probe system for use in stereotactic neurosurgery.

FIG. 2 shows a multi-electrode probe system 20 for use in performing neurosurgery. The system includes a conventional micromanipulator 21 that mounts on a stereotactic frame 25 bolted to the patient's head 23. A typical micromanipulator 21 includes a stepper motor that accurately positions the probe in the patient's brain. The micromanipulator 21 moves the probe 10 in increments that often are as small as 1 $\mu$m.

The system 20 also includes an analog or digital processor 22 that receives the signals from the probe 10 via the conductive cable 19 and derives information useful to the neurosurgeon. The processor 22 records this information in an optional storage device 24 and provides this information to the neurosurgeon on an optional video display 26 or through another output device, as described below. The processor 22 also receives information from the micromanipulator 21 indicating the probe's position in the brain, or "brain depth," with respect to a predetermined reference position.

In stereotactic neurosurgery, the surgeon typically needs to know the "spike rate" generated by individual neurons. A neuron's spike rate indicates the number of current spikes occurring in a brain cell during a given time period, usually measured in terms of spikes per second. Because an electrode often detects signals from multiple neurons, and because several electrodes often detect signals generated by a single neuron, the processor performs an optional spike sorting algorithm to determine which neurons generated which of the detected spikes. Examples of suitable spike sorting algorithms are described in the following documents, the entire disclosures of which are incorporated by reference: U.S. Provisional Application 60/099,184, filed on Sep. 4, 1998, by Andersen, Pezaris, and Sahani, and entitled "Probabilistic Algorithms for the Separation of Signals in Neural Microelectrode Recordings"; and Sahani, et al., "On the Separation of Signals from Neighboring Cells in Tetrode Recordings," Advances in Neural Information Processing Systems 10 (1998). The processor 22 stores all of this information in the storage device 24 and, in some embodiments, indexes the stored information with the brain depth of the site from which the information was derived.

Figure 3:
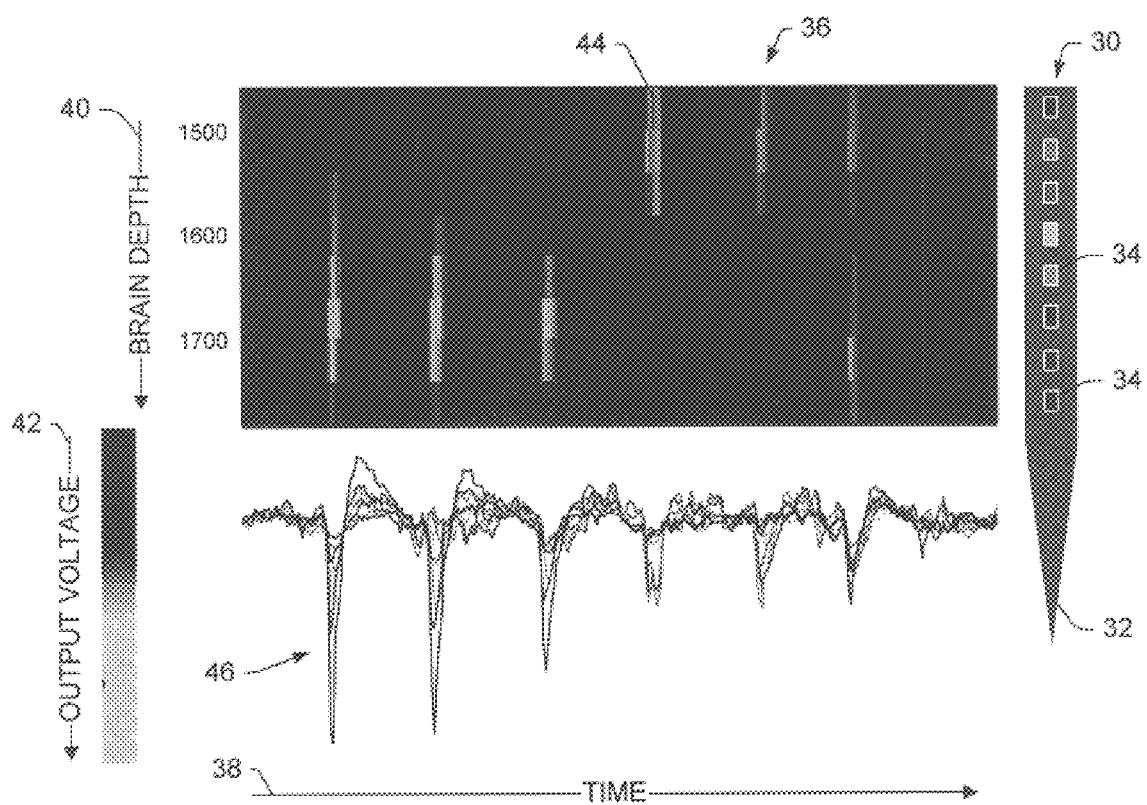
FIG. 3 is an example of a visual display provided by the system of FIG. 2 during neurosurgery.

FIG. 3 is one example of the type of information that is presented on the video display 26. The information in this example is derived from a probe 30 having a single shaft 32 with eight evenly-spaced electrodes 34. The information is presented in the form of a color-coded graph 36 that provides information on three axes: a horizontal axis 38 representing time; a vertical axis 40 representing brain depth; and a color axis 42 representing signal voltage, or level of neuronal activity. At each position on the horizontal (time) axis 38, the graph 36 includes a color-coded box 44 for each of the electrodes 34 on the probe 30. The position of the box 44 along the vertical (depth) axis 40 indicates the depth of the corresponding electrode in the brain. The color of the box 44 indicates the magnitude of the voltage detected by the corresponding electrode. In this example, lighter colors indicate larger detected voltages. In some implementations, the display includes traces 46 showing the instantaneous values of the signals produced by the electrodes 14A–14J. These traces are similar to the oscilloscope traces traditionally used by surgeons in performing stereotactic neurosurgery.

Figure 4:
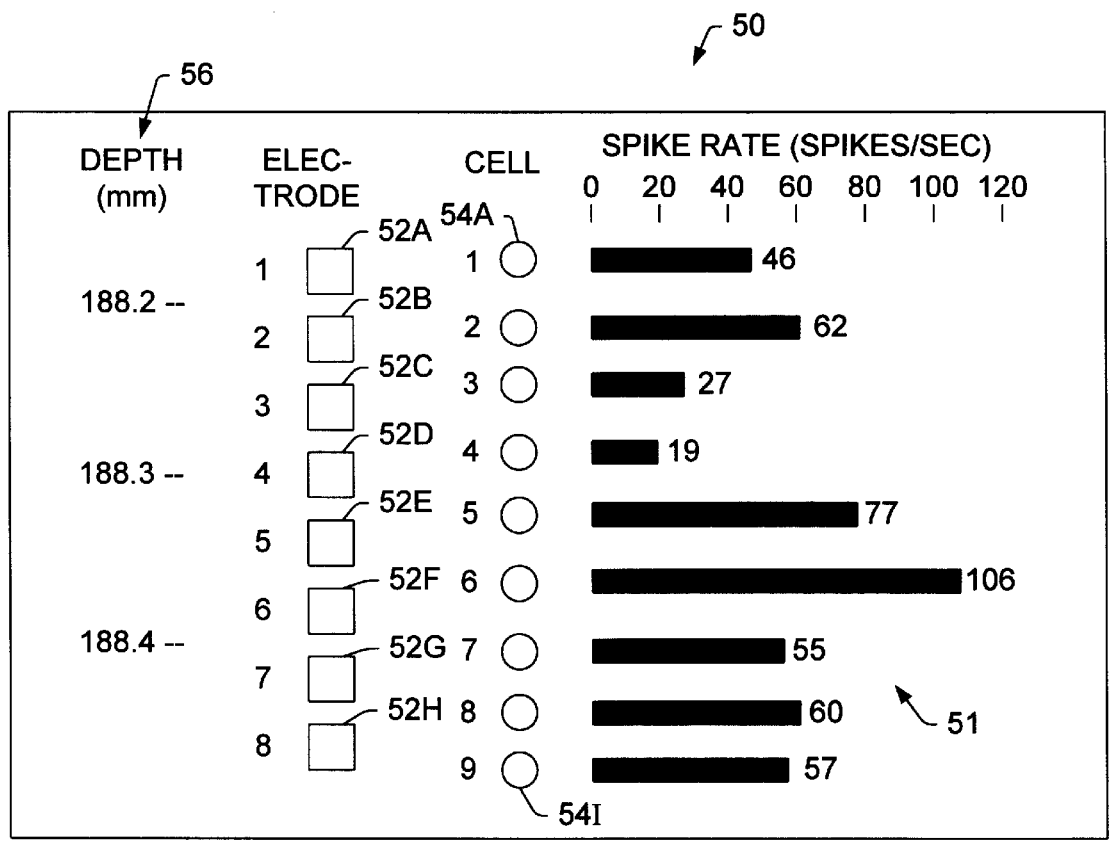
FIG. 4 is another example of a visual display provided by the system of FIG. 2 during neurosurgery.

FIG. 4 is another example of the type of information that is presented on the video display 26. In this example, the display 50 provides a histogram 51 indicating the spike rates of nine individual brain cells, as detected by a probe with eight electrodes. The display 50 includes a set of icons 52A–H representing the eight electrodes. These icons 52A–H are arranged spatially in a manner that represents the positions of the electrodes on the probe. The display 50 also includes a set of icons 54A–I representing the nine brain cells. These icons 54A–I are arranged in a manner that represents the approximate spatial orientation of the brain cells, as determined by the spike sorting algorithm in evaluating the strengths of the signals produced by the electrode array. The display 50 also displays an indication 56 of the brain depth at which the electrodes and the brain cells are located. When a conventional micromanipulator is used, these values indicate the distance between the corresponding portion of the probe and the reference point.

During surgery, the neurosurgeon uses conventional techniques, such as CT and MRI scans, to locate the general area in which target site lies. The surgeon then inserts an appropriately designed multi-electrode probe into the brain and positions the probe near the target area. Once in the brain, the electrodes produce signals that indicate the presence of activity in nearby neurons. For a pallidotomy procedure, the target site lies within the Globus pallidus internus.

Neurons in the Gpi typically fire at spike rates greater than 60 spikes per second, while neurons in the Gpe typically fire at rates between 30–60 spikes per second. The display identifies the boundary between the Gpi and the Gpe by showing where the spike rate changes significantly. For some types of neurosurgery, the surgeon stimulates a particular portion of the brain, e.g., by moving one of the patient's limbs, to intensify the differences in spike rate between two adjacent areas of the brain.

Other embodiments are within the scope of the following claims. For example, some systems present neuronal activity information to the surgeon in a non-visual manner, such as through audible signals that change in tone as the level of neuronal activity changes. In some cases, each of the electrodes is mapped to a unique sound, which allows the surgeon to distinguish changes in activity at one electrode from changes at other electrodes. These sound-based systems free the surgeon's eyes to focus on the probe itself and on other video-based equipment. Other embodiments use virtual reality equipment, such as 3D goggles and data gloves, to indicate the level of neuronal activity. Data gloves give non-visual information about neuronal activity by supplying sensory feedback to the fingers of the person wearing the gloves. Moreover, while the invention has been described in terms of neuronal spike analysis, other techniques for monitoring neuronal activity and other types of information are useful as well.

What is claimed is:

1. A method of using a multi-electrode probe during stereotactic neurosurgery, the method comprising:

inserting a multi-electrode probe into an area of a brain that includes a target site to be treated, where the probe includes multiple electrodes on a plurality of shafts that produce output signals corresponding to neuronal activity at multiple sites in the brain; and generating audible output based on the electrode output signals to provide an indication of a level of concurrent neuronal activity at each of the multiple sites in the brain, wherein each electrode's output is mapped to a unique audible output.

2. The method of claim 1, further comprising generating from the electrode output signals graphical output that provides a depth profile indicating the level of concurrent neuronal activity at various depths in the brain.

3. The method of claim 2, wherein the graphical output provides an indication of spike rate for individual neurons at the multiple sites.

4. The method of claim 2, wherein the graphical output includes a visual indication of the level of neuronal activity at each of the multiple sites.

5. The method of claim 2 wherein the graphical output is presented in a user interface.

6. The method of claim 1, further comprising providing a stimulus directed to neurons at the target site to increase the level of neuronal activity at the target site.

7. The method of claim 1, further comprising selecting a probe that is tailored for use in the identified area of the brain.

8. The method of claim 1 further comprising, prior to inserting the multi-electrode probe, identifying the area of the brain that includes the target site to be treated.

9. The method of claim 1 wherein the output signals produced by the electrodes include information corresponding to different depth and width locations in the brain.

10. A multi-electrode probe system for use during stereotactic neurosurgery, the system comprising:

a multi-electrode probe adapted to be inserted into an area of a brain that includes a target site to be treated through stereotactic neurosurgery, where the probe includes multiple electrodes on a plurality of shafts that produce output signals corresponding to neuronal activity at multiple sites in the brain;

a processor that receives the output signals from the electrodes and derives a level of neuronal activity that occurs at each of the multiple sites; and an output device that produces audible output based on the electrode output signals to provide an indication of the level of concurrent neuronal activity at each of the multiple sites in the brain, wherein each electrode's output is mapped to a unique audible output.

11. The system of claim 10, further comprising a user interface that provides a depth profile indicating the level of concurrent neuronal activity at various depths in the brain.

12. The system of claim 11, wherein the user interface includes a visual display of the level of neuronal activity detected by each of the electrodes at multiple time slots.

13. The system of claim 12, wherein the visual display provides a color coded indicator of the level of neuronal activity.

14. The system of claim 10, wherein the probe is tailored for use in the identified area of the brain.

15. The system of claim 10, wherein the probe includes micromachined silicon electrodes.

16. The system of claim 10 wherein the output signals produced by the electrodes include information corresponding to different depth and width locations in the brain.

17. A method of using a multi-electrode probe during stereotactic neurosurgery, the method comprising:

producing a plurality of electrode output signals corresponding to neuronal activity at a plurality of sites in a brain by inserting a multi-electrode probe into an area of the brain; and providing an audible indication of a level of concurrent neuronal activity at the plurality of sites by generating a unique audible output for each electrode based on the produced electrode output signals.

18. The method of claim 17 wherein the electrode output signals include information corresponding to different depth and width locations in the brain.

19. The method of claim 17 further comprising generating from the electrode output signals graphical output that provides a depth profile indicating the level of concurrent neuronal activity at various depths in the brain.

20. The method of claim 17 wherein the graphical output provides an indication of spike rate for individual neurons at the plurality of sites.

21. The method of claim 17 wherein the graphical output includes a visual indication of the level of neuronal activity at each of the plurality of sites.

22. The method of claim 17 further comprising providing a stimulus directed to neurons at the target site to increase the level of neuronal activity at the target site.

23. The method of claim 17 further comprising selecting a probe that is tailored for use in the identified area of the brain.

* * * * *